United States Patent [19]
Page et al.

[11] Patent Number: 5,059,536
[45] Date of Patent: Oct. 22, 1991

[54] MUTANT STRAINS OF AZOTOBACTER VINELANDII USED FOR THE HYPERPRODUCTION OF POLY-β-HYDROXYBUTYRATE DURING EXPONENTIAL GROWTH

[75] Inventors: William J. Page, Edmonton, Canada; Olga Knosp, Innsbruck, Austria

[73] Assignee: The Governors of the University of Alberta, Edmonton, Canada

[21] Appl. No.: 631,211

[22] Filed: Dec. 21, 1990

Related U.S. Application Data

[63] Continuation of Ser. No. 268,789, Nov. 9, 1988, abandoned.

[30] Foreign Application Priority Data

Nov. 7, 1988 [CA] Canada ................................ 582405

[51] Int. Cl.$^5$ ............................................. C12R 1/065
[52] U.S. Cl. ............................. 435/252.3; 435/135; 435/170; 435/252.1; 435/831
[58] Field of Search .................... 435/135, 170, 252.1, 435/252.3, 831

[56] References Cited

U.S. PATENT DOCUMENTS 3,036,959  5/1962  Baptist .
4,358,583  11/1982  Walker et al. ...................... 435/135
4,477,654  10/1984  Holmes et al. .
4,808,535  2/1989  Isbister ............................. 435/252.1

FOREIGN PATENT DOCUMENTS 0052459  5/1982  European Pat. Off. .
0114086  7/1984  European Pat. Off. ............. 435/135
63-198991  8/1988  Japan ................................ 435/135

OTHER PUBLICATIONS

Chem. ABS vol. 78 (1973) 43960r Fukasawa et al. Tetrahedron 1972 28(21) 5359-5365.
Stockdale et al., "Occurrence of Poly-B-Hydroxybutyrate in the Azotobacteriaceae", J. Bacteriology (1968), 95:1798-1803.
Senior et al., "The Role of Oxygen Limitation in the Foundation of Poly-B-hydroxybutyrate During Batch ad Continuous Culture of Azotobacter Beijerinckii", Biochem. J. (1972), 128:1193-1201.
Ward et al., "Effect of Oxygen and Nitrogen Limitation on Poly-B-Hydrobutyrate Biosynthesis in Ammonium-Grown Azotobacter Beijerinckii", J. Gen. Microbiol. (1977), 102:61-68.
King, "Biotechnology, An Industrial View", J. Chem. Tech. Biotechnol. (1982), 32:2-8.
Howells, "Single-cell Protein and Related Technology", Chemistry and Industry, Aug. 7, 1982.
Byrom, "Polymer Synthesis by Microorganisms: Technology and Economics", Trends in Biotechnol. (1987), pp. 246-250.
"Recombinant Industrial Polymers: Feasible for Special Applications", Genetic Technology News, Mar. 1987, pp. 6-7.
Griffin et al., "Plastic and Synthetic Fibres from Microorganisms: A Dream or a Potential Reality?," Microbiol. Sci. (1987), 4:357-361.
Page, "Genetic Transformation of Molybdenum-Starved Azotobacter vinelandii: Increased Transformation Frequency and Recipient Range", Can. J. Microbiol. (1985), 31:659-662.
Davis et al., "Microbiology", Harper & Row Publishers, Hagerstown, pp. 20-21.
Fukasawa et al., "Structure of the Yellow-Green Fluorescent Peptide Produced by Iron-Deficient Azotobacter Vinelandii Strain O", Tetrahedron, (1972) 8:5359-5365.
Page et al., "Hyperproduction of Poly-beta-hydroxybutyrate During Exponential Growth of Azotobacter Vinelandii UWD", Appl. Environ. Microbiol. (1989), 55:1334-1339.

Primary Examiner—Herbert J. Lilling
Attorney, Agent, or Firm—Banner, Birch, McKie & Beckett

[57] ABSTRACT

A mutant strain of *Azotobacter vinelandii* exhibits hyperproduction of poly-β-hydroxybutyrate during its growth.

5 Claims, 2 Drawing Sheets

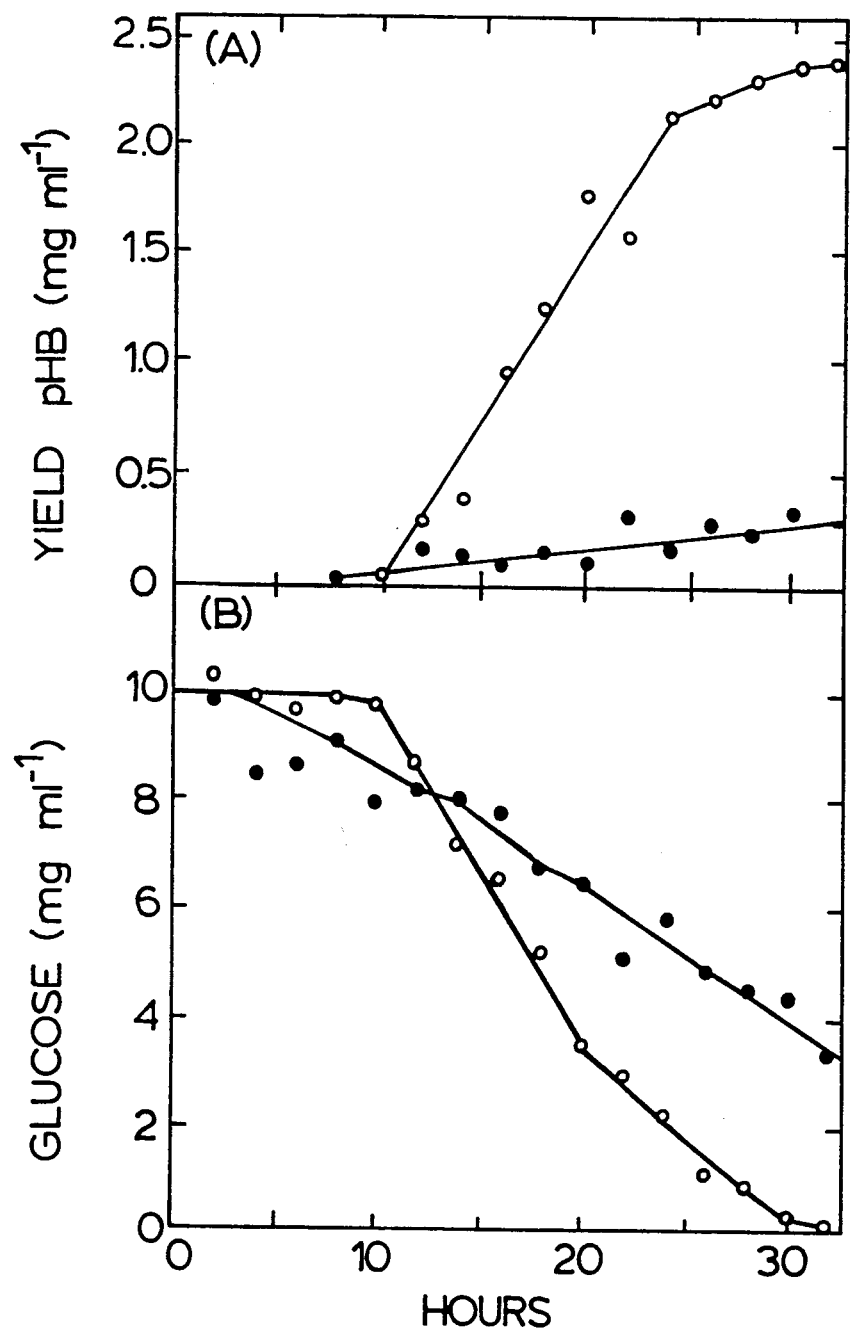

MUTANT STRAINS OF AZOTOBACTER VINELANDII USED FOR THE HYPERPRODUCTION OF POLY-β-HYDROXYBUTYRATE DURING EXPONENTIAL GROWTH

This application is a continuation of application Ser. No. 07/268,789, filed Nov. 9, 1988 and now abandoned.

FIELD OF THE INVENTION

This invention relates to the hyperproduction of poly-β-hydroxybutyrate during growth of mutant strains of *Azotobacter vinelandii*.

BACKGROUND OF THE INVENTION

Poly-β-hydroxybutyrate (pHB) is a biodegradable, biocompatible, thermoplastic made by microorganisms [Baptist, J. N., 1962, U.S. Pat. No. 3,036,959]. In the cell, pHB is an intracellular storage material synthesized and accumulated during unbalanced growth. It accumulates as distinct white granules that are clearly visible in the cytoplasm of the cell. Under conditions of nutrient starvation, pHB is used by the cell as an internal reserve of carbon and energy. Many bacteria including those in the soil, are capable of pHB production and breakdown. Animal cells do not form pHB but are able to break down the polymer.

pHB is a homopolymer of repeating 3-hydroxybutyric acid units. Copolymers with hydroxyvaleric acid can be made by "precursoring" (e.g.) adding propionic acid to the culture during growth [Holmes et al., 1981, European Patent 0,052,459 and 1984 U.S. Pat. No. 4,477,654]. This modification to the pHB homopolymer reduces the crystallinity and melting point of the plastic, allowing film formation and melt-extrusion applications. PHB plastics also are used in microelectronics applications exploiting the piezoelectric properties of pHB. An immediate market for pHB plastics will be in high value added products (e.g.) biodegradable surgical pins, plates, pegs and sutures, implants for drug delivery, and possibly meshes can be used as artificial skin materials. PHB derived plastics also have considerable potential application as biodegradable bulk plastics, replacing non-biodegradable products formed from polypropylene or polyethylene. Development of many of these products is ongoing in view of their potential uses.

Production of pHB in the cell occurs during imbalanced growth. Usually this is the stationary phase of bacterial growth, but this can be induced in an actively growing culture by imposing a nutrient ($O_2$, nitrogen, phosphate, or sulfate) limitation in the presence of excess carbon source. During this imbalance, NADH accumulates and exerts a feedback repression on various enzymes whose activities are essential for the continued growth of the cell. NADH can be oxidized to $NAD^+$, eliminating this growth inhibition, by the action of acetoacetyl CoA reductase and the polymerization of acetoacetyl CoA into pHB.

$NAD^+$ is nicotinamide adenine dinucleotide and NADH is its reduced form. $NAD^+$ is a major electron acceptor in the oxidation of fuel molecules in the cell. $NAD^+$ fulfils this function by accepting two electrons and two hydrogen ions from substances it oxidizes. Thus, $NAD^+$ becomes NADH. Stryer, Biochemistryk 2d ed., W. H. Freeman and Company, San Francisco, pp. 244-246.

*Azotobacter vinelandii* is a harmless soil microbe that has an obligate $O_2$ requirement for growth and can use $N_2$ as a nitrogen source via nitrogen fixation. *A. vinelandii* normally produces pHB by the methods noted above and much of the early work concerning pHB synthesis was conducted in Azotobacter species. Azotobacter species that produce large amounts of pHB have been reported, but these cells have been unstable and also produce large amounts of capsule and slime, which interfere with pHB extraction and decrease the efficiency of conversion of carbon substrate to pHB.

At present, pHB is produced commercially by ICI in the U.K., using a strain of *Alcaligenes eutrophus* growing in a glucose salts medium. Their fermentation involves a rapid growth phase (60 h), followed by phosphate-limitation and glucose feeding (an additional 48-60 h). During phosphate-limited growth, pHB is formed and may account for 75% of the total cell weight. The yield per liter is dependent on the initial cell mass and theoretical yields of 0.33 t pHB $t^{-1}$ glucose have been calculated [Byrom, D., Trends in Biotechnology 5: 246-250, 1987].

Presently, pHB production involves a long fermentation time, in the stationary phase of growth, to obtain high levels of pHB. Different nutrient limitations have been imposed during stationary phase to enhance pHB production.

Currently, pHB production is limited by a relatively long fermentation time, dependance on amount of pHB produced upon continued cell activity after the active (exponential) phase, dependance on amount of pHB produced upon a pregrowth period to achieve an initial cell mass such that a certain amount of the carbon source is used to produce cell mass rather than pHB, and the need to use relatively expensive substrates (such as glucose) for fermentation.

To date, there appears to have been an effort to increase pHB yield in industrial applications by increasing batch size. Because pHB is considered a secondary metabolite, produced in the stationary phase of growth after active cell growth, the possibility of increasing yield by bringing about pHB production during exponential growth has not been addressed and successfully exploited.

Likewise, the possibility of exploiting relatively unrefined carbon sources in pHB production has not been successfully exploited. The unrefined carbon sources are typically more complex, less refined, or sometimes unpurified materials or even mixtures of materials, which are not necessarily of pure or defined composition. Example of unrefined carbon sources include blackstrap molasses, sugar-beet molasses, carbohydrates and phenols in industrial or municipal wastes. Instead of said unrefined substances, relatively pure carbon sources of defined composition, such as glucose have been used for industrial pHB production to date.

SUMMARY OF THE INVENTION

According to an aspect of the invention, a genetically transformed microorganism of the species *Azotobacter vinelandii* has the identifying characteristics of ATCC 53799.

According to another aspect of the invention, a biologically pure culture of a genetically transformed microorganism of the species *Azotobacter vinelandii*, the genetically transformed microorganism having the identifying characteristics of ATCC 53799, when cultured is capable of producing pHB in a recoverable quantity upon fermentation in an aqueous nutrient medium containing assimilable nutrients.

According to another aspect of the invention, a genetically transformed bacterium of the species *Azotobacter vinelandii*, the genetically transformed bacterium having the identifying characteristics of:

i) extremely abundant pHB granules in cells;
   ii) dense white colonies of cells;
   iii) very turbid culture which reaches an $O.D._{620}$ of 10 and looks like cow's milk after 24 hours of growth;
   iv) no formation of substantial capsule or slime. According to another aspect of the invention, a process for producing pHB comprises:

i) culturing genetically transformed bacteria of the species *Azotobacter vinelandii*, said genetic transformants having the identifying characteristics of ATCC 53799 in a culture medium having a source of assimilable nutrients; and ii) recovering pHB from said bacteria.

BRIEF DESCRIPTION OF THE DRAWINGS

FIG. 2 is a plot comparing *Azotobacter vinelandii* strain UW ATCC 13705( ) with respect to production of pHB (plot A) and consumption of glucose (plot B) during growth. The information depicted in FIG. 2 is derived from analyses performed on the cells and culture fluids from FIG. 1.

DETAILED DESCRIPTION OF THE PREFERRED EMBODIMENTS

Figure 1:
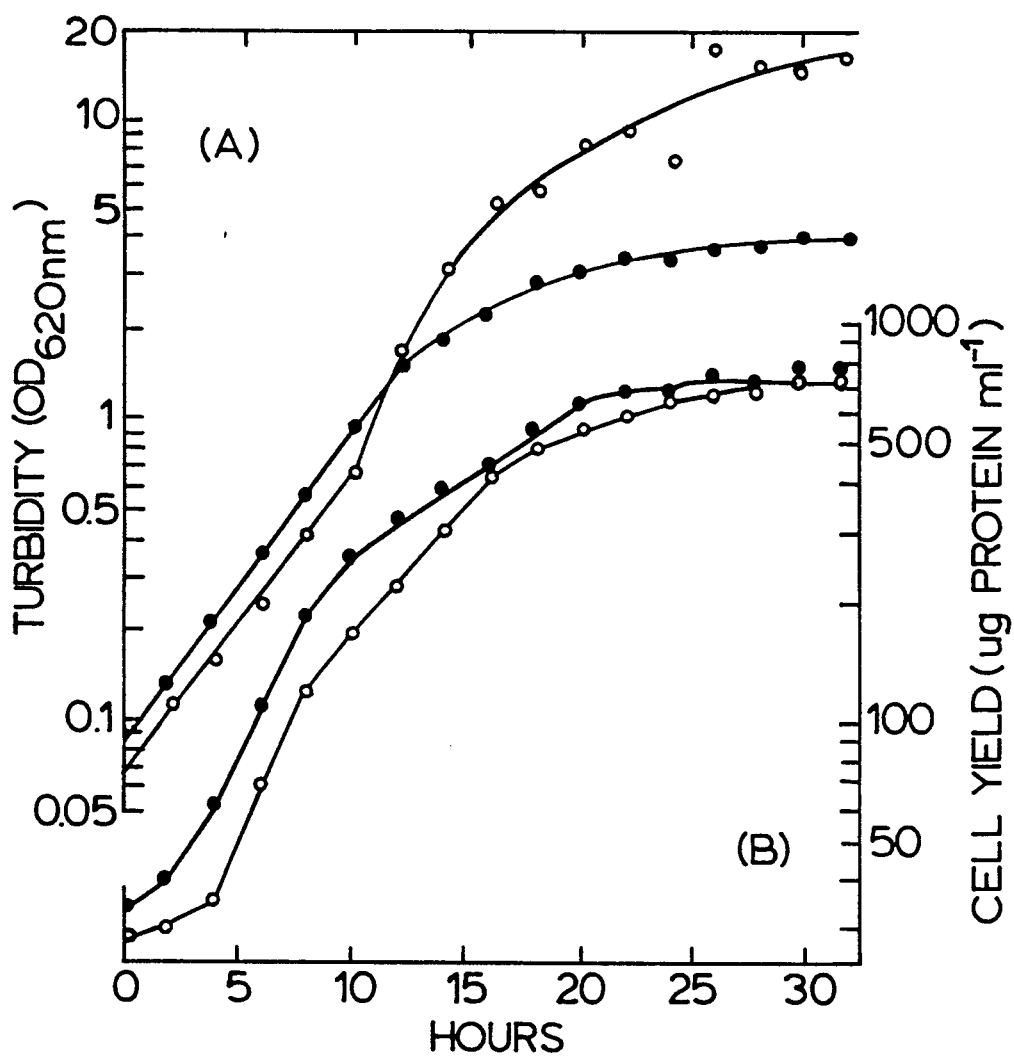
FIG. 1 is a plot comparing *Azotobacter vinelandii* strain UW ATCC 13705( ) and *Azotobacter vinelandii* kstrain UWD ATCC 53799(○) with respect to increase in turbidity (plot A) and protein content (plot B) during incubation at 30° C. with vigorous aeration.

The bacterial transformant, according to this invention, which for the purpose of reference in the detailed description is identified as UWD, was derived from the species *Azotobacter vinelandii*. It is understood that the invention encompasses not only the particular UWD, but all derivatives thereof and other related microorganisms having similar taxonomic descriptions. The Azotobacter genus is described in Bergey's manual of Determinative Bacteriology, Vol. 1., pp. 219–229, 1984, N. R. Krieg and J. G. Holt (ed.), Williams and Wilkins, Baltimore, and J. P. Thompson and V. B. D. Skerman, 1979. Azotobacteraceae: The taxonomy and ecology of the aerobic nitrogen-fixing bacteria, Academic Press, New York, pp. 168–69, pp. 178–79.

*Azotobacter vinelandii* wild-type, which for the purpose of reference in the detailed description is identified as OP, is readily available and has been investigated by various groups. *Azotobacter vinelandii* OP is deposited at American Type Culture Collection under accession number ATCC 13705. It is understood that throughout the specification, the generally accepted nomenclature "ATCC" for the American Type Culture Collection will be used. ATCC is located at 12301 Parklawn Drive, Rockville, Md. 20852. All deposits at ATCC are given accession numbers which are referred to throughout the specification. The University of Wisconsin subculture of *Azotobacter vinelandii* OP is identified as UW for the purpose of reference in the detailed description. The UWD transformant, according to this invention, was developed and isolated by transforming UW cells with DNA prepared from the mutant *Azotobacter vinelandii* ATCC 53800 (which for the purpose of reference in the detailed description is identified as strain 113) such as defined in the following Example. It is appreciated that there are many techniques available for inducing such mutation and that there are many techniques available for transforming bacterial cells or otherwise changing their genetic composition and such other techniques are contemplated herein although not specifically exemplified.

The isolated genetic transformant has been characterized in the following Examples and has been deposited at the American Type Culture Collection. The deposit was made on August 10, 1988 under accession number ATCC 53799. The taxonomical characteristics of the UWD strain are as follows.

The UWD strain shares characteristics with strain UW (OP, ATCC 13705) except that it forms excess pHB during exponential growth, it is resistant to rifampicin (20 $\mu$g/ml), it has a white colony colour, and it forms the fluorescent-green pigment under iron-sufficient conditions.

Basic characteristics: Large ovoid cells, Gram-negative, pleomorphic ranging from rods to cocci. The cells are motile by peritrichous flagella, substantial capsules are not formed and the cells form fragile cysts only after very long incubation (several months to a year). Growth is strictly aerobic and nitrogen is fixed aerobically. Substrate utilization characteristics have been well defined and agree with Bergey's Manual of Determinative Bacteriology, Vol. 1, pp. 219–229, 1984. N. R. Krieg and J. G. Holt (ed.), Williams and Wilkins, Baltimore, and J. P. Thompson and V. B. D. Skerman, 1979. Azobacteraceae: The taxonomy and ecology of the aerobic nitrogen-fixing bacteria, Academic Press, New York, pp. 168–69, pp. 178–179.

The taxonomic description of strain 113 is as follows.

This strain is derived from *A. vinelandii* ATCC 12837 by NTG mutagenesis. It shares characteristics with ATCC 12837 except it is resistant to rifampicin (20 $\mu$g/ml) and it forms poly-$\beta$-hydroxy-butyrate (pHB) during exponential growth.

Basic characteristics: Large ovoid cells, Gram-negative, pleomorphic ranging from rods to cocci. The cells are motile by peritrichous flagella, form capsules and form cysts in older cultures. Iron-limited cultures produce a fluorescent yellow-green pigment. Growth is strictly aerobic and nitrogen is fixed aerobically. Substrate utilization characteristics have been well defined and agree with Bergey's Manual of Determinative Bacteriology, Vol. 1, pp. 219–229, 1984, N. R. Krieg and J. G. Holt (ed.), Williams and Wilkins, Baltimore, and J. P. Thompson and V. B. D. Skerman, 1979. Azotobacteraceae: The taxonomy and ecology of the aerobic nitrogen-fixing bacteria, Academic Press, New York, pp. 168–69, pp. 178–79.

The UWD transformant was developed and isolated in accordance with the following preferred method. Cells of strain UW, were obtained from the Department of bacteriology at University of Wisconsin. This strain of cells is a capsule-negative wild-type, which were genetically transformed with DNA prepared from cells of strain 113 *Azotobacter vinelandii* 53800, which is a rifampin-resistant strain derived by NTG mutagenesis of the capsule-positive strain ATCC 12837.

Strain 113 ATCC 53800 was produced by exposing *Azotobacter vinelandii* strain ATCC 12837 to 100 $\mu$g/ml N-methyl-N'-nitro-N-nitrosoguanidine (NTG) in Burk buffer, pH 7.2, for 30 min. Survivors were plated on Burk medium containing 1% glucose, 1.8% agar and 20 $\mu$g rifampin/ml. Strain 113 was, therefore, selected as a nitrogen-fixing, rifampin-resistant strain of ATCC 12837. The hyper-production of pHB by strain 113 was an unselected mutation that also had occurred during the NTG mutagenesis procedure.

DNA for transformation was prepared as a crude lysate material. A thick suspension of strain 113 was prepared in 15 mM saline-15 mM sodium citrate buffer, pH 7.0, containing 0.05% sodium dodecyl sulfate. This suspension was heated at 60° C. for 60 min. in a waterbath. When cool, this lysate containing crude (unpurified) DNA was used directly in transformation assays. Optimal conditions for generation of competent strain UW (or *Azotobacter vinelandii* in general) which can take up this crude DNA, are documented in Page and von Tigerstrom, 1978. Can. J. Microbiol. 24:1590–1594. Optimal conditions for the transformation of these competent cells by the crude DNA are documented in Page and Von Tigerstrom, 1979. J. Bacteriol. 139:1058–1061.

The preferred procedure used to transform UW cells with strain 113 DNA is described in Page, W. J. 1985. Can. J. Microbiol. 31: 659–662. While almost any strain of *Azotobacter vinelandii* can be transformed by strain 113 DNA, the most successful transformations for the purpose of producing maximal amounts of readily extractable pHB are the transformations of capsule-negative strains. Of these, *Azotobacter vinelandii* strain OP ATCC 13705 is a readily available strain held in culture collections. The strain that was transformed to create the UWD transformant was strain UW, the University of Wisconsin copy of strain OP.

Transformation of strain UW with strain 113 DNA results in a rifampin-resistance transformation frequency of about $1.0 \times 10^{-4}$ to $8.7 \times 10^{-3}$ per viable cell plated (i.e. at best 8.7 transformants per 1000 cells plated). This is a readily reproducible frequency of transformation. Of these rifampin-resistant colonies, about 13% appeared to have streaks of white or white sectors within the normal pinkish-tan cell mass. When these sectoring colonies were restreaked, they gave rise to sectoring colonies and dense white colonies at a ratio of about 1:1. The dense white colonies were then selected and designated UWD. This procedure and these results are reproducible and will readily generate UWD cells.

UWD is readily separated from the UW stock because UWD is resistant to rifampin and UW is not resistant. Therefore, on plates containing solid medium and 20 μg rifampin/ml, only colonies of UWD (or other rifampin resistant cells) will grow.

The separation of pHB hyperproducing cells from the general population of transformed cells is readily replicable, because the sectoring colony phenotype is quite distinctive and upon subculture it readily generates solid white colonies. Non-hyperproducing cells result in pinkish-tan colonies under the same conditions.

Quite surprisingly it was discovered that a certain number of so transformed cells produced dense-white colonies, rather than the normal translucent tan wild-type colonies of the UW strain. The cells from these dense colonies (the UWD cells) were packed with pHB granules, while the wild-type (strain UW) contained only a few small granules of pHB.

It is believed that in theory the superior production of pHB in the mutant is due to a genetic defect in strain 113 and the UWD cells concerning the NADH oxidase that normally recycles NAD+ via respiratory oxidation of NADH. As a result of this defect, the cell accumulates NADH and must turn-on pHB synthesis in order to grow. Therefore, pHB is formed during active (balanced; exponential) growth, the exact opposite of the normal conditions promoting pHB formation in the wild-type. Although this theory appears to be borne out by the examples, it is understood that the principles of the invention should not be limited to this theory.

Because pHB is formed during exponential growth, conditions which enhance growth also increase pHB formation. For example, vigorous aeration (rather than $O_2$-limitation) promotes faster use of glucose and faster production of pHB. Nitrogen-fixing UWD cells also produce pHB.

Strain 113 also produces large amounts of pHB, but also produces large amounts of capsule and slime. The UWD cells do not form substantial capsule and slime and therefore only convert the bulk of the sugar into cell mass (like strain UW) and pHB.

Solid media for the maintenance of cultures contained 1.5 to 1.8% (w/v) agar.

Various Carbon sources were added to the culture medium at 1 to 5% (w/v) concentration. pHB production was best with reduced hexose, mono and disaccharide carbon sources (glucose, sucrose, maltose) or with sodium gluconate or glycerol, and was much lower with more oxidized or short-chain carbon sources (acetate, ethanol). Glucose and sucrose are relatively expensive refined substrates for pHB production. Sucrose does not have to be "inverted" before use by the UWD cells but fructose is poorly used for pHB production. Because pHB formation is not dependent on nutrient limitation, cheaper unrefined carbon sources can be used by the UWD cells. Good production of pHB has been obtained using 2% (w/v) corn syrup, sugar-beet molasses, blackstrap and cooking molasses, and more refined grades of refiner's molasses. The UWD cells grow well in media containing at least 5% (w/v) molasses or corn syrup, however, the yield of pHB $ml^{-1}$ is not greater than that obtained with 2 or 3% molasses or corn syrup. On these impure carbon sources the wild-type strains did not produce detectable or significant amounts (<0.1 mg/ml) of pHB. Use of these unrefined carbon sources can result in a significant reduction in production costs.

The nitrogen source used in the cell culture is preferably $N_2$ (from air) or ammonium acetate at 1.1 to 2.2 g/L.

Production of pHB was demonstrated in batch cultures. The volumes of culture producing optimal yields of pHB were in the range 20–50% culture volume: flask or vessel volume with rotary shaking (to increase aeration and mixing) at 175 to 300 rpm (normally 250 rpm was used). Incubation temperatures were found to be 30°–35° C. for optimal yields.

Various aspects of the invention are demonstrated in the following examples.

EXAMPLE 1 pHB was formed and extracted from cultures of the UWD transformant as follows. The growth medium in which UWD cells were cultured to yield pHB was a minimal salts medium composed of g/L: $KH_2PO_4$, 0.2; $K_2HPO_4$, 0.8; $MgSO_4 \cdot 7H_2O$, 0.2; $CaSO_4 \cdot 2H_2O$, 0.1: $FeSO_4 \cdot 7H_2O$, 0.005; $Na_2MoO_4 \cdot 2H_2O$, 0.00025; at a pH 7.2.

When UWD cells were grown in the described minimal salts medium initially containing 10 mg $ml^{-1}$ $C_6H_{12}O_6$, the medium became very turbid and by 24 h reached an $O.D._{620}$ of 10 and looked like cow's milk as shown in FIG. 1. This Figure is comparison of the UW ATCC 13705 strain ( ) and the UWD ATCC 53799 strain (◯) for increase in turbidity (A) and protein content (B) during incubation at 30° C. with vigorous aeration. In the same time period, strain UW attained an $O.D._{620}$ of 3 and produced a tan colored suspension as shown in FIG. 1.

Analysis of the growth of the cultures showed that the UWD cells (a) formed pHB as soon as they started using glucose, (b) formed pHB during exponential growth, (c) used the glucose in the medium faster than strain UW, (d) produced 2 mg pHB ml$^{-1}$ in 24h, compared to 0.25 mg pHB ml$^{-1}$ produced by strain UW under the same conditions as shown in FIG. 2.

In the analysis, pHB was isolated by the method of Law and Slepecky, 1961. J. Bacteriol 82: 33-36. Cells containing pHB were collected by centrifugation and dissolved in bleach for 1 h at 40° C. The residue was washed with distilled water, 95% ethanol and acetone. The dry weight of the residue was then determined. The residue was 100% soluble in chloroform, which solubility is characteristic of pHB. Selected samples were also subjected to the colorimetric assay described by Law and Slepecky to further confirm that the residue was pHB. The dry weight of the cells before extraction was determined after concentration by centrifugation and washing twice with distilled water to remove media contaminants.

EXAMPLE 2

The effect of different carbon sources on pHB production by the UWD strain was investigated. Various carbon sources were evaluated where the selected source of nitrogen was either ammonia or $N_2$. The results of the investigation are itemized in the following Table 1.

TABLE 1

Influence of different carbon sources on pHB production by *A. vinelandii* strain UWD.

| Medium[c] | Ammonium-grow[a] pHB mg ml$^{-1}$ | Nitrogen-fixing[b] pHB mg ml$^{-1}$ |
|---|---|---|
| 1% Glucose | 1.88 | 1.86 |
| 30 mM Acetate[d] | 0.09 | 0.08 |
| 1% Glucose + 30 mM acetate[d] | 2.05 | 1.27 |
| 1% Maltose | 2.08 | 1.09 |
| 2% Sucrose | 0.96 | 1.44 |
| 1% Ethanol | 0.17 | 0.03 |
| 1% Glycerol | 1.27 | 0.11 |

[a]All cultures contained 15 mM ammonium acetate.
[b]All cultures contained $N_2$ as sole-N source.
[c]Cultures were grown with vigorous aeration at 30° C. for 24 h.
[d]Total acetate concentration

EXAMPLE 3

The investigations of Example 2 were extended to consider the impact of less expensive carbon sources on pHB. The results of this investigation are summarized in the following Table 2.

TABLE 2 pHB production by *A. vinelandii* strain UWD using corn syrup and molasses carbon sources.

| Carbon source[a] | pHB mg ml$^{-1}$ | % pHB [cell dry weight]$^{-1}$ |
|---|---|---|
| 1% Glucose | 2.48 | 60 |
| 1% Sucrose | 2.39 | 68 |
| 1% Fructose | 0.64 | 53 |
| 2% Corn Syrup | 2.38 | 57 |
| 2% Black Strap Molasses | 2.33 | 54 |
| 2% Cooking Molasses | 2.49 | 54 |
| 2% Refiner's Molasses | 2.40 | 56 |
| 2% Sugar-Beet Molasses | 2.58 | 60 |

[a]Salt medium plus 15 mM ammonium acetate, incubated at 30° C. with vigorous aeration for 24 h. Molasses media were adjusted to pH 7.0 with NaOH.

Although preferred embodiments of the invention are described herein in detail, it will be understood by those skilled in the art that variations may be made thereto without departing from the spirit of the invention or the scope of the appended claims.

We claim:

1. A biologically pure culture of a mutant microorganism of claim 4 having all the identifying characteristics of ATCC 53799, said identifying characteristics of ATCC 53799 including the hyperproduction of pHB in recoverable quantities during the exponential growth of said mutant microorganism.

2. A biologically pure culture of a mutant microorganism of claim 4 having all the identifying characteristics of ATCC 53799, said culture being capable of hyperproducing pHB in a recoverable quantity upon fermentation in an aqueous nutrient medium containing assimilable nutrients, said hyperproduction of pHB occurring during the exponential growth of said mutant microorganism.

3. A microorganism of claim 2, which microorganism is capable of producing pHB in a recoverable quantity upon fermentation in an aqueous nutrient medium containing assimilable nutrients, comprising unrefined carbon sources of a type or types suitable to maintain said microorganism and to be used by said microorganism to hyperproduce pHB in a recoverable quantity during the exponential growth of said mutant microorganism.

4. A biologically pure culture of a mutant microorganism of the species *Azotobacter vinelandii*, said mutant having the identifying characteristics:
  i) produces cells containing extremely abundant pHB granules in culture;
  ii) forms dense white colonies of cells in solid culture;
  iii) after 24 hours of growth in liquid culture, forms a very turbid culture which reaches an $O.D._{620}$ of 10 and looks like cow's milk;
  iv) during exponential growth, hyperproduces pHB but does not product substantial amounts of capsules and does not produce substantial amounts of slime.

5. A culture of claim 4 wherein said mutant is a transformation of *Azotobacter vinelandii* ATCC 13705.

* * * * *

UNITED STATES PATENT AND TRADEMARK OFFICE
CERTIFICATE OF CORRECTION

PATENT NO. : 5,059,536

DATED : October 22, 1991

INVENTOR(S) : PAGE, et al

It is certified that error appears in the above-identified patent and that said Letters Patent is hereby corrected as shown below:

Column 3, line 23, please change "13705(o)" to --13705(●)--;

line 24, "kstrain" should be --strain--;

line 28, please change "13705(o) to --13705(●)--; and add the following after 13705(●): "and Azotobacter vinelandii strain USD ATCC 53799(o)".

Column 7, line 3, change "(o) to --(●)--.

Signed and Sealed this

Twenty-fourth Day of August, 1993

Attest:

*Attesting Officer*

BRUCE LEHMAN

*Commissioner of Patents and Trademarks*